US010933146B2

(12) United States Patent
Jasanoff et al.

(10) Patent No.: US 10,933,146 B2
(45) Date of Patent: Mar. 2, 2021

(54) CELL-PERMEABLE IMAGING SENSORS AND USES THEREOF

(71) Applicant: Massachusetts Institute of Technology, Cambridge, MA (US)

(72) Inventors: Alan Pradip Jasanoff, Cambridge, MA (US); Ali Barandov, Brookline, MA (US); Benjamin B. Bartelle, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/218,155

(22) Filed: Dec. 12, 2018

(65) Prior Publication Data

US 2019/0184036 A1     Jun. 20, 2019

Related U.S. Application Data

(60) Provisional application No. 62/597,875, filed on Dec. 12, 2017.

(51) Int. Cl.
*A61K 49/00* (2006.01)
*A61K 49/08* (2006.01)
*A61K 49/10* (2006.01)
*G01N 33/68* (2006.01)

(52) U.S. Cl.
CPC ........ *A61K 49/085* (2013.01); *A61K 49/0002* (2013.01); *A61K 49/103* (2013.01); *G01N 33/6872* (2013.01)

(58) Field of Classification Search
CPC ............................. A61K 49/00; A61K 49/085
See application file for complete search history.

(56) References Cited

U.S. PATENT DOCUMENTS

| 5,578,498 | A | 11/1996 | Singh et al. | |
|---|---|---|---|---|
| 6,770,261 | B2 * | 8/2004 | Meade | A61K 49/085 424/1.11 |
| 7,504,088 | B2 | 3/2009 | Riley et al. | |
| 2002/0127181 | A1 * | 9/2002 | Edwards | A61K 51/0497 424/1.65 |
| 2004/0208827 | A1 | 10/2004 | McMurray et al. | |
| 2008/0138292 | A1 | 6/2008 | Zhang et al. | |

OTHER PUBLICATIONS

Deán-Ben et al., Functional optoacoustic neuro-tomography for scalable whole-brain monitoring of calcium indicators. Light Sci Appl. Dec. 2, 2016;5(12):e16201. doi: 10.1038/lsa.2016.201. 7 pages.
Roberts et al., Calcium sensor for photoacoustic imaging. J Am Chem Soc. Feb. 28, 2018;140(8):2718-21. Epub Sep. 25, 2017.
International Search Report and Written Opinion dated Mar. 25, 2019 for Application No. PCT/US2018/065196.
Adams et al., Biologically useful chelators that take up calcium $^{(2+)}$ upon illumination. J Am Chem Soc. 1989;111(20):7957-68. Epub Sep. 1989.
Angelovski et al., Smart magnetic resonance imaging agents that sense extracellular calcium fluctuations. ChemBioChem. Jul. 21, 2008;9(11):1729-34. doi: 10.1002/cbic.200800165.
Atanasijevic et al., Calcium-sensitive MRI contrast agents based on superparamagnetic iron oxide nanoparticles and calmodulin. Proc Natl Acad Sci U S A. Oct. 3, 2006;103(40):14707-12. Epub Sep. 26, 2006.
Bal et al., Oxidation of α,β-unsaturated aldehydes. Tetrahedron 1981;37(11-D): 2091-6.
Barandov et al., Membrane-permeable Mn(III) complexes for molecular magnetic resonance imaging of intracellular targets. J Am Chem Soc. May 4, 2016;138(17):5483-6. doi: 10.1021/jacs.5b13337. Epub Apr. 18, 2016.
Barandov et al., Sensing intracellular calcium ions using a manganese-based MRI contrast agent. Nat Commun. 2019;10:897(1-9). Epub Feb. 22, 2019.
Bartelle et al., Molecular fMRI. J Neurosci. Apr. 13, 2016;36(15):4139-48. doi: 10.1523/JNEUROSCI.4050-15.2016.
Chen et al., Possible mechanisms underlying the biphasic regulatory effects of arachidonic acid on $Ca^{2+}$ signaling in HEK293 cells. Cell Signal. Aug. 2012;24(8):1565-72. doi: 10.1016/j.cellsig.2012.03.016. Epub Mar. 30, 2012.
Chen et al., Imaging neural activity using Thy1-GCaMP transgenic mice. Neuron. Oct. 18, 2012;76(2):297-308. doi: 10.1016/j.neuron.2012.07.011. Epub Oct. 17, 2012.
DeLeon-Rodriguez et al., Responsive MRI agents for sensing metabolism in vivo. Acc Chem Res. Jul. 21, 2009;42(7):948-57. doi: 10.1021/ar800237f. Epub Mar. 6, 2009.
Ghosh et al., Probing the brain with molecular fMRI. Curr Opin Neurobiol. Jun. 2018;50:201-210. doi: 10.1016/j.conb.2018.03.009. Epub Apr. 9, 2018.
Grynkiewicz et al., A new generation of $Ca^{2+}$ indicators with greatly improved fluorescence properties. J Biol Chem. Mar. 25, 1985;260(6):3440-50.
Heffern et al., Lanthanide probes for bioresponsive imaging. Chem Rev. Special Issue: 2014 Bioinorganic Enzymology. Apr. 23, 2014;114(8):4496-539. doi: 10.1021/cr400477t. Epub Dec. 13, 2013.
Ishii et al., Light generation of intracellular $Ca^{2+}$ signals by a genetically encoded protein BACCS. Nat Commun. Aug. 18, 2015;6:8021(1-15). doi: 10.1038/ncomms9021.
Johnson, The Molecular Probes Handbook: A Guide to Fluorescent Probes and Labeling Technologies, 11$^{th}$ Ed. ThermoFisher Scientific. Waltham, MA 2010. 965 pages.
Lee et al., In vivo imaging with a cell-permeable porphyrin-based MRI contrast agent. Chem Biol. Jun. 25, 2010;17(6):665-73. doi: 10.1016/j.chembiol.2010.05.009.
Li et al.., A Calcium-sensitive magnetic resonance imaging contrast agent. J Am Chem Soc. 1999;121(6):1413-4. Epub Jan. 29, 1999.

(Continued)

*Primary Examiner* — Michael G. Hartley
*Assistant Examiner* — Jagadishwar R Samala
(74) *Attorney, Agent, or Firm* — Wolf, Greenfield & Sacks, P.C.

(57) ABSTRACT

The disclosure relates in some aspects to imaging agents, and in particular, imaging agents for sensing of calcium signaling. According to some embodiments of the disclosure, contrast agents for magnetic resonance imaging and related technologies are provided, and methods of making and using the contrast agents.

20 Claims, 8 Drawing Sheets

(56) References Cited

OTHER PUBLICATIONS

Moussaron et al., Ultrasmall nanoplatforms as calcium-responsive contrast agents for magnetic resonance imaging. Small. Oct. 7, 2015;11(37):4900-9. doi: 10.1002/smll.201500312. Epub Jul. 14, 2015.

Okada et al., Calcium-dependent molecular fMRI using a magnetic nanosensor. Nat Nanotechnol. Jun. 2018;13(6):473-477. Suppl Info, 2 pages. doi: 10.1038/s41565-018-0092-4. Epub Apr. 30, 2018.

Ouzounov et al., In vivo three-photon imaging of activity of GCaMP6-labeled neurons deep in intact mouse brain. Nat Methods. Apr. 2017;14(4):388-390. doi: 10.1038/nmeth.4183. Epub Feb. 20, 2017. Advance online publication, 5 pages.

Paxinos et al., The Rat Brain in Stereotaxic Coordinates, Compact 3rd Ed. Academic Press: San Diego, CA. 1997. 25 pages.

Que et al., Responsive magnetic resonance imaging contrast agents as chemical sensors for metals in biology and medicine. Chem Soc Rev. Jan. 2010;39(1):51-60. doi: 10.1039/b914348n. Epub Oct. 7, 2009.

Ruiz et al., On the mechanism of stimulation of H+ transport in gastric mucosa by Ca++ ionophore A23187. II. Ca++-cyclic AMP interactions. Cell Calcium. Oct. 1983;4(4):267-79.

Somjen, Extracellular potassium in the mammalian central nervous system. Annu Rev Physiol. 1979;41:159-77.

Tian et al., Selective esterase-ester pair for targeting small molecules with cellular specificity. PNAS. Mar. 27, 2012;109(13):4756-61.

Tong et al., HEK-293 cells possess a carbachol- and thapsigargin-sensitive intracellular $Ca^{2+}$ store that is responsive to stop-flow medium changes and insensitive to caffeine and ryanodine. Biochem J. Oct. 1, 1999;343 Pt 1:39-44.

Tsien et al., Measurement of cytosolic free $Ca^{2+}$ in individual small cells using fluorescence microscopy with dual excitation wavelengths. Cell Calcium. Apr. 1985;6(1-2):145-57.

Tsien et al., Calcium homeostasis in intact lymphocytes: cytoplasmic free calcium monitored with a new, intracellularly trapped fluorescent indicator. J Cell Biol. Aug. 1982;94(2):325-34. Epub Aug. 1, 1982.

Wang, Prospects of photoacoustic tomography. Med Phys. Dec. 2008;35(12):5758-67.

* cited by examiner

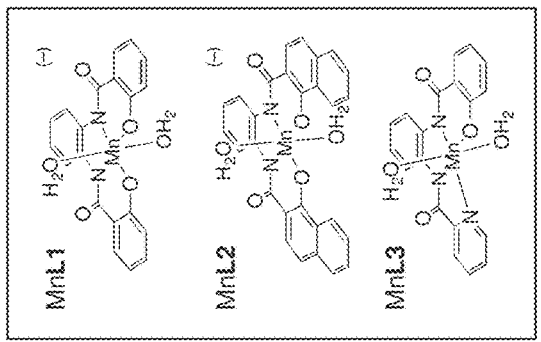
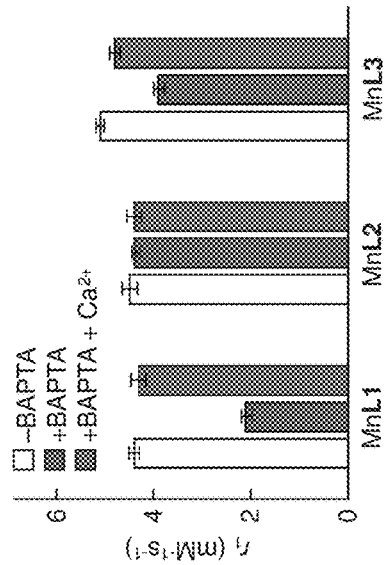
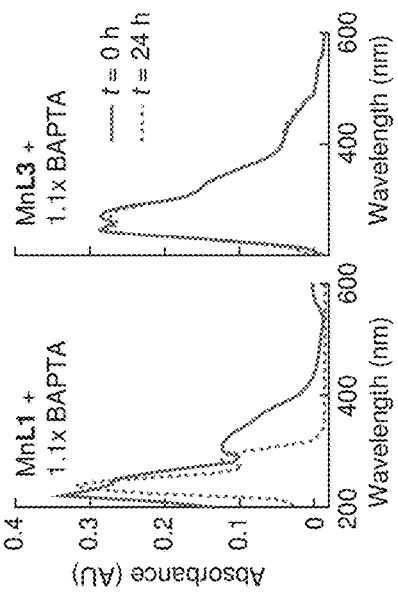
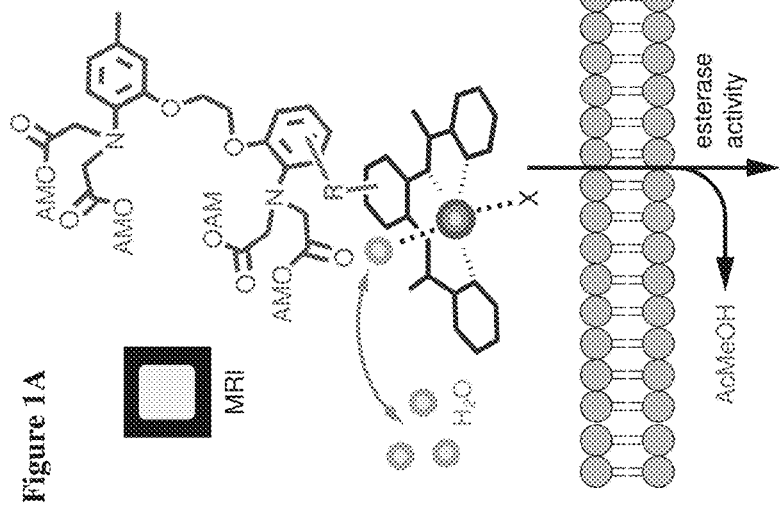
Figure 1A
Figure 1B
Figure 1C
Figure 1D

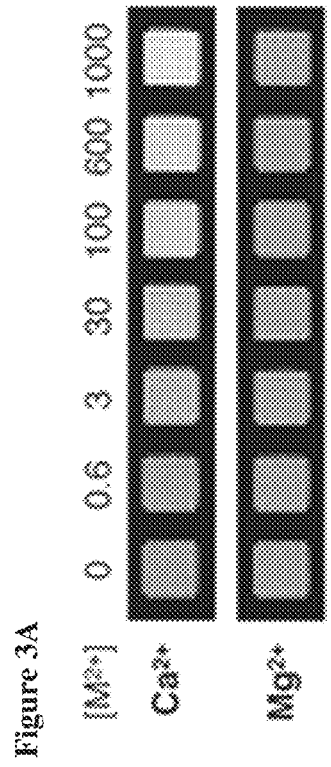
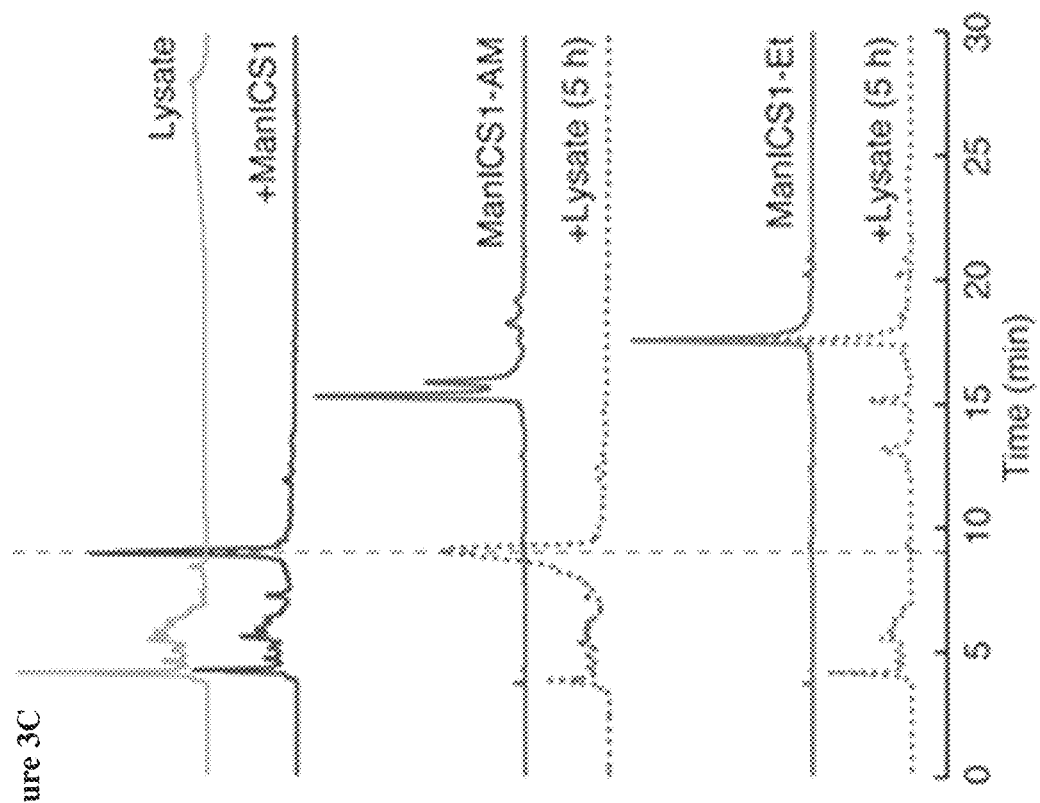
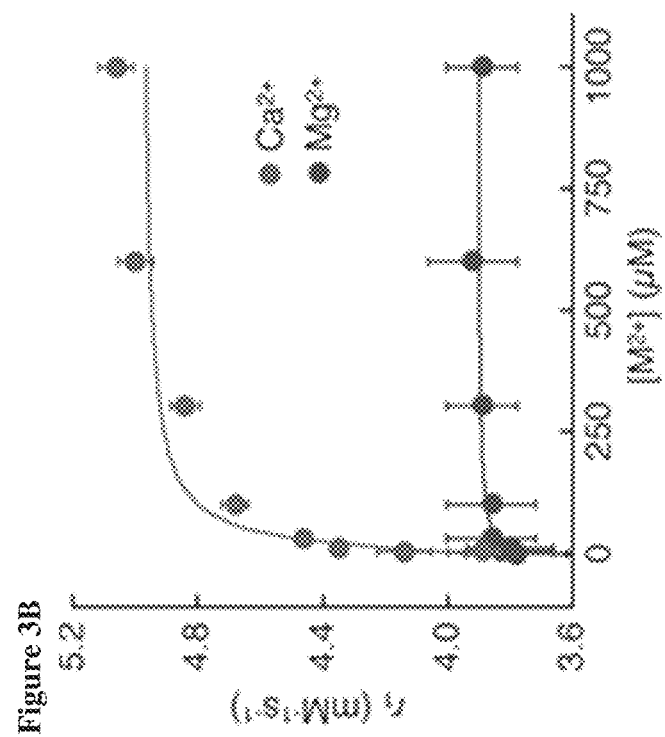
Figure 3A
Figure 3B
Figure 3C

ManICS1-AM (R = CH₃COOCH₂, AM)
ManICS1 (R = H)

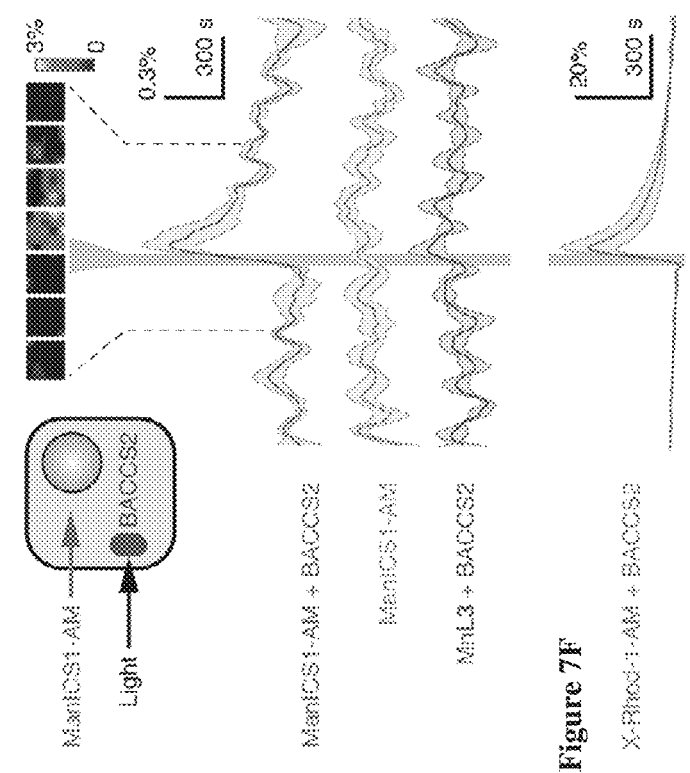
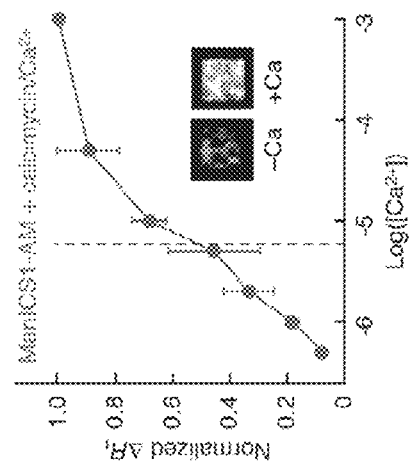
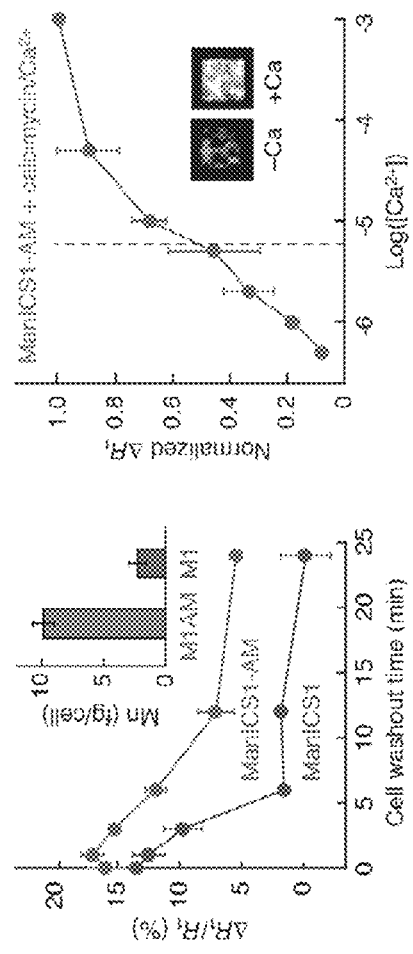
Figure 7A, Figure 7B, Figure 7C, Figure 7D, Figure 7E, Figure 7F

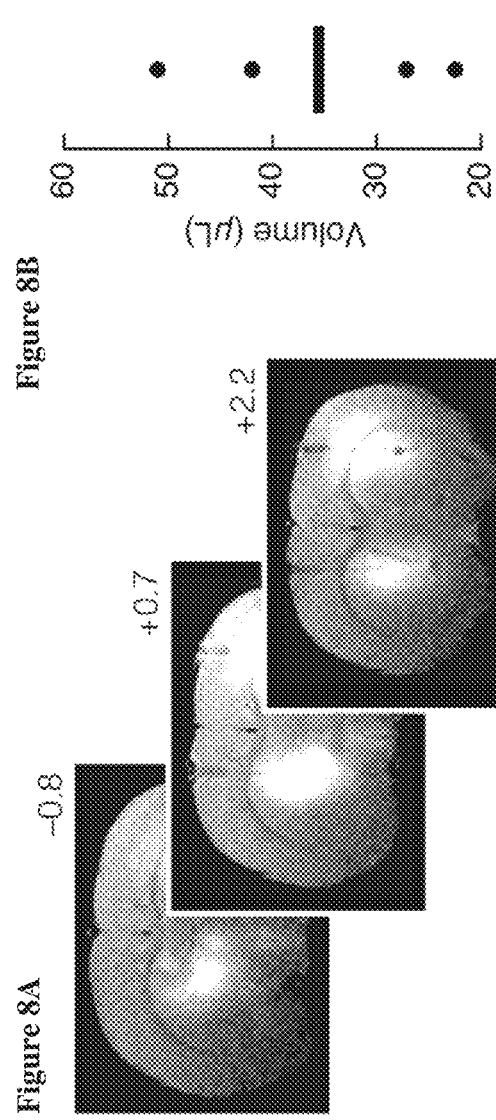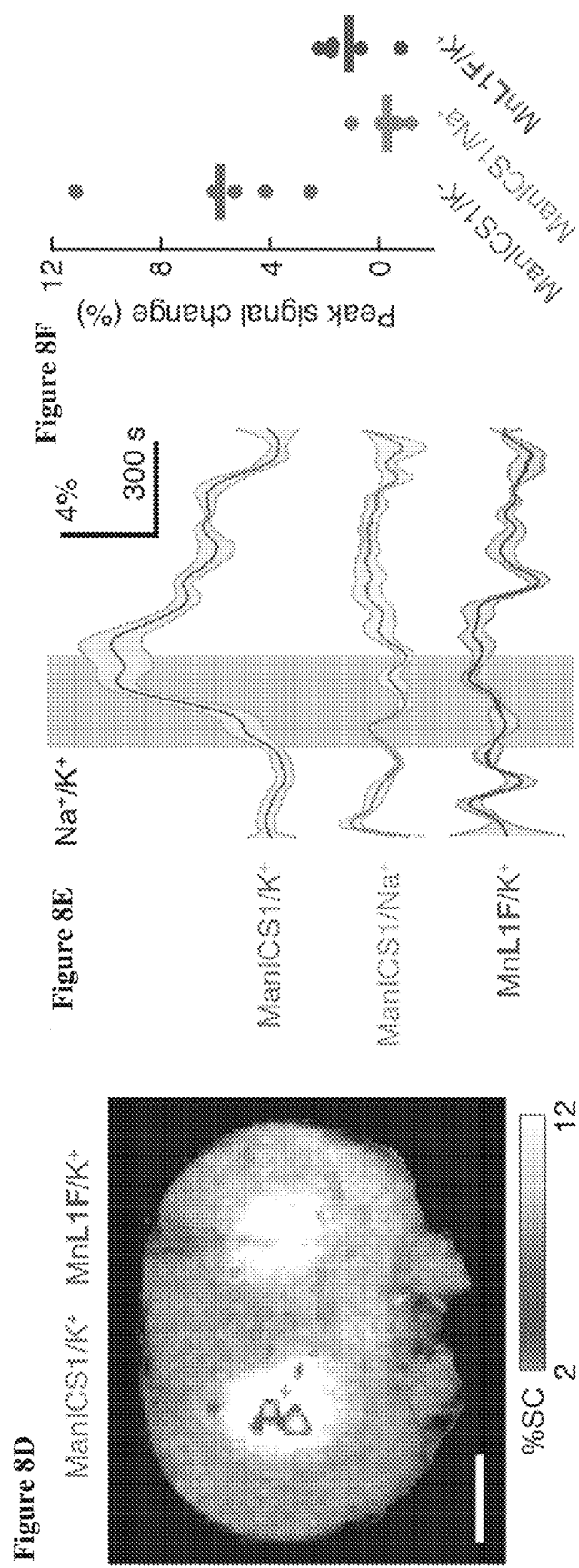

US 10,933,146 B2

CELL-PERMEABLE IMAGING SENSORS AND USES THEREOF

RELATED APPLICATIONS

This application claims priority under 35 U.S.C. § 119(e) to U.S. Provisional Application No. 62/597,875, filed Dec. 12, 2017 and entitled "CELL-PERMEABLE IMAGING SENSORS AND USES THEREOF," which is incorporated herein by reference in its entirety for all purposes.

GOVERNMENT FUNDING

This invention was made with Government support under Grant Nos. R01 DA038642 and U01 NS090451 awarded by the National Institutes of Health. The Government has certain rights in the invention.

FIELD OF THE INVENTION

The invention relates in some aspects to imaging agents.

BACKGROUND OF THE INVENTION

Available imaging techniques for measuring large-scale signaling dynamics in intact organisms have been limited. With optical techniques it is possible to perform functional imaging of signaling dynamics at depths of up to about two millimeters in tissue, but for most vertebrate species this only represents a small fraction of the volumes of experimental interest. Implantable endoscopes and prisms permit measurements in deeper structures, but only over limited fields of view. Hybrid techniques like photoacoustic tomography achieve submillimeter imaging resolution with considerably greater tissue penetration than conventional optics. Thus, imaging techniques are often limited by sharp trade-offs between depth and resolution.

SUMMARY OF THE INVENTION

Aspects of the disclosure relate to sensors and related methods for imaging. In some embodiments, cell-permeable imaging sensors are provided that facilitate imaging of cellular ion signaling (e.g., calcium signaling). In some embodiments, magnetic resonance imaging (MRI) provides a powerful technique for evaluating ion signaling (e.g., calcium ion) in animals and humans (e.g., in wide-field, deep-tissue context) using the sensors provided herein. In some embodiments, MRI achieves a combination of unlimited depth penetration, relatively high 3D spatial resolution (<100 µm in some contexts), and sensitivity to a wide variety of contrast mechanisms. Accordingly, in some aspects, novel magnetic resonance imaging (MRI) sensors are disclosed herein. In some embodiments, these sensors are specific for detecting ions in cells, such as calcium ions. In some embodiments, the sensors provided herein may be applied to noninvasive neuroimaging, muscular (including cardiac) imaging, immunological activation, or imaging of secretory cells in other organs of animals and humans. Furthermore, in some embodiments, sensors provided herein are powerful tools for functional MRI (MRI) and have various applications, including but not limited to: functional visualization of brain activity in healthy and disease/disordered models at preclinical studies, neuroimaging relevant to surgical planning, peripheral neuroimaging relevant to significant neuropathies, tests of cardiac or skeletal muscle function, and monitoring lymphatic function in inflammation and cancer.

In some aspects, an ion sensor (e.g., calcium sensor) reported herein comprises a small-molecule complex comprising a transition metal (e.g., manganese). In some embodiments, the small-molecule complex comprises a lipophilic, branched chelating moiety complexed with a transition metal. In some embodiments, the lipophilic, branched chelating moiety is linked to an analyte binding moiety (e.g., a cell-permeable calcium chelator such as BAPTA) (See, e.g., FIG. 5). In some embodiments, the sensor comprises ManICS1 (see, e.g., FIG. 2, 16). In some embodiments, the sensor comprises the structure in FIG. 2, 13. In some embodiments, the sensor comprises ManICS1-AM (see, e.g., FIG. 2, 14). In some embodiments, micromolar concentrations of ManICS1-AM cause enhancement of T1-weighted MRI signal. In some embodiments, ManICS1-AM accumulates and is retained cytosolically in cells and upon enzymatic reaction turns into its active form ManICS1. In some embodiments, cells loaded with ManICS1-AM undergo stimulus-induced changes in T1-weighted MRI contrast that parallel responses measured optically using a fluorescent calcium indicator.

In some aspects, a sensor comprising the structure, Y-L-Z is provided. In some embodiments, Y is an analyte binding moiety (e.g., that binds calcium ions). In some embodiments, Z is a lipophilic, branched chelating moiety. In some embodiments, L is a linker that covalently links Y and Z.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 1A to 1D depict cell permeable sensors for calcium-dependent molecular fMRI. FIG. 1A shows a cell permeable paramagnetic platform (complex, molecule portion below —R—, Mn-PDA candidate complexes shown at top right), a BAPTA-based calcium chelator (molecule portion above —R—), and a linker connecting them (—R—). Prior to cell entry (top) the BAPTA carboxylates were protected with cleavable acetoxymethyl (AM) esters, and water ($H_2O$) exchange was hypothesized to take place at the paramagnetic metal center (circle at center of paramagnetic platform), leading to $T_1$-weighted MRI signal enhancement (labeled MRI). When the agent entered cells (bottom left), the AM esters were cleaved, liberating the sensor in its calcium-free "off" state; in this state, water exchange may be blocked by interactions between the BAPTA moiety and $Mn^{3+}$, leading to low MRI signal. When calcium bound to the sensor (bottom right), the MRI signal increased again as interactions between the BAPTA and paramagnetic platform were reduced. FIG. 1B depicts results of an evaluation of interactions between BAPTA and Mn-PDA contrast agents. In the absence of BAPTA, the $Mn^{3+}$ complexes did not produce calcium-dependent $T_1$-weighted MRI contrast changes (top), but in the presence of 1.1 eq BAPTA, both MnL1 and MnL3 displayed sensitivity to the addition of calcium (bottom). FIG. 1C depicts longitudinal relaxivity ($r_1$) values corresponding to the conditions in FIG. 1B. FIG. 1D depicts optical spectra of contrast agents MnL1 and MnL3 in the presence of BAPTA after incubation for 0 h (solid) or 24 h (dashed), indicating comparative stability of MnL3.

FIGS. 3A to 3C show that ManICS1 reported calcium-dependent MRI signal changes in buffer, and that MnICS1-AM underwent enzymatic hydrolysis. FIG. 3A shows $T_1$-weighted images of ManICS1 with addition of varying micromolar concentrations of $CaCl_2$ (top) or $MgCl_2$ (bottom) in MOPS buffer, pH 7.4. FIG. 3B shows relaxivity changes for Calcium (top curve) and Magnesium (bottom curve) corresponding to conditions in FIG. 3A. Ligand-depleting bimolecular binding models were used to generate the fitted curves shown. FIG. 3C shows reversed phase HPLC traces of 10% (v/v) HEK293 cell lysate (Lysate), ManICS1(+ManICS1), ManICS1-AM, ManICS1-AM treated with cell lysate for 5 h (+Lysate (5 h) directly below ManICS1-AM), ManICS1-Et, and ManICS1-Et treated with cell lysate for 5 h (+Lysate (5 h) directly below ManICS1-Et). Vertical dashed line indicates expected elution time of ManICS1.

FIG. 4A shows a washout time course of $\Delta R_1/R_1$ vs. time for HEK293 cells preincubated with ManICS1-AM (top) or ManICS1 acid form (bottom). ManICS1-AM was selectively retained, e.g., which may occur due to intracellular cleavage of its AM esters. FIG. 4B shows compartment-specific accumulation of manganese in cells incubated with ManICS1-AM and ManICS1, showing enhanced labeling of both cytosolic (left of each set of three) and membranous (right of each set of three) fractions, as indicated by inductively coupled plasma optical emission spectrometry (ICP-OES) of fractionated labeled cells. FIG. 4C shows calcium responses measured in HEK293 cells labeled with ManICS1-AM (left plot) or Fura-2-AM (right plot) and treated with cell stimulants thapsigargin (Th), carbachol (Ch), the $Ca^{2+}$ ionophore calcimycin (Ca), or arachidonic acid (AA). MRI responses diagrammed at left paralleled fluorescence responses measured under equivalent conditions at right. FIG. 4D shows titration of extracellular calcium concentration in the presence of calcimycin in ManICS1-AM-loaded cells. A midpoint of calcium-induced changes occurred at $[Ca^{2+}]=5$ micromolar ($\mu$M). Inset compares MRI scans of cell pellets imaged in the absence (left) vs. presence (right) of calcium.

FIGS. 7A to 7F show that ManICS1 reports calcium-dependent MRI signal changes in cells. FIG. 7A shows the washout time course of $\Delta R_1/R_1$ vs. time for HEK293 cells preincubated with 10 $\mu$M ManICS1-AM or ManICS1 acid form. Elemental analysis of cytosolic fractions from incubated cell lysates (inset) indicates intracellular manganese accumulation in ManICS1-AM (M1AM)-treated cells but not ManICS1 (M1)-treated cells. FIG. 7B shows titration of extracellular calcium concentration equilibrated in the presence of 10 $\mu$M of the $Ca^{2+}$ ionophore calcimycin in ManICS1-AM-loaded cells. A midpoint of calcium-induced changes occurs at $[Ca^{2+}]=5$ $\mu$M. Inset compares MRI scans of cell pellets imaged in the absence (left) vs. presence (right) of 1 mM calcium. FIG. 7C shows calcium responses measured from HEK293 cells labeled with ManICS1-AM and treated by extracellular addition of chemical stimulants (left). Significant $R_1$ changes were observed in response to calcimycin (Ca) and arachidonic acid (AA) ($p\leq0.001$), but not thapsigargin (Th) or carbachol (Ch) ($p\geq0.2$). FIG. 7D shows responses measured by fluorescence spectroscopy from cells loaded with the fluorescent calcium indicator Fura-2FF-AM under stimulation conditions as in FIG. 7C. FIG. 7E shows cells were loaded by incubation with 40 $\mu$M ManICS1-AM, transfected with the light sensitive Orai calcium channel activator BACCS2, and stimulated with 480 nm light (diagram at left). The top time course shows resulting changes in the $T_1$-weighted signal as a function of time before, during, and after stimulation (vertical gray bar). Inset at top depicts image snapshots binned over successive 240 s windows during the time series portion indicated by dashed lines and indicating percent signal changes observed at a voxel level. Stimulus-dependent signal changes were not observed in analogous experiments performed using cells lacking BACCS2 (middle) or cells labeled with MnL3 instead of ManICS1-AM (bottom). FIG. 7F shows fluorescence time course observed from BACCS2-expressing cells incubated with 5 $\mu$M X-Rhod-1-AM and stimulated as in FIG. 7E.

FIGS. 8A to 8F show ManICS1-AM enables detection of neural activation in rat brain. FIG. 8A shows $T_1$-weighted MRI showing broad contrast enhancement following infusion of 15 $\mu$L ManICS-1 (left) or calcium-insensitive control agent (MnL1F, right) into rat striatum. Rostrocaudal coordinates with respect to bregma indicated. FIG. 8B shows estimated volume of signal enhancements within 10% of peak values after ManICS1-AM infusion in four animals (mean=36±7 $\mu$L). In FIG. 8C, a plot of peak MRI signal in ManICS1-AM infused brain regions over time shows a mean signal enhancement of 20±2% with an average of 0.9% signal decrease per hour with respect to image intensity in unenhanced tissue (bold); the signal decrease from 30 to 90 minutes post-infusion was not statistically significant (t-test p=0.42, n=6). Data from individual animals shown in gray. FIG. 8D shows 1 $\mu$L $K^+$ infusion causes $T_1$-weighted MRI signal increases in the presence of predelivered ManICS1-AM (left) but not MnL1F (right). Average peak signal change across multiple animals (n=5) is indicated by the color scale superimposed on a high resolution $T_1$-weighted image of a representative rat. Scale bar=3 mm. FIG. 8E shows the region of interest analysis, which shows the time course of signal changes observed during $K^+$ or $Na^+$ in the presence of ManICS1 (top and middle, respectively), and during $K^+$ stimulation in the presence of calcium-insensitive MnL1F (bottom). FIG. 8F shows MRI signal changes observed in individual animals within one minute of $K^+$ or $Na^+$ treatment offset for the conditions in FIG. 8E. Mean signal changes observed during potassium stimulation in the presence of ManICS1-AM was significantly greater than results from both controls (t-test p≤0.016, n=5).

DETAILED DESCRIPTION OF CERTAIN EMBODIMENTS OF THE INVENTION

Figure 2:
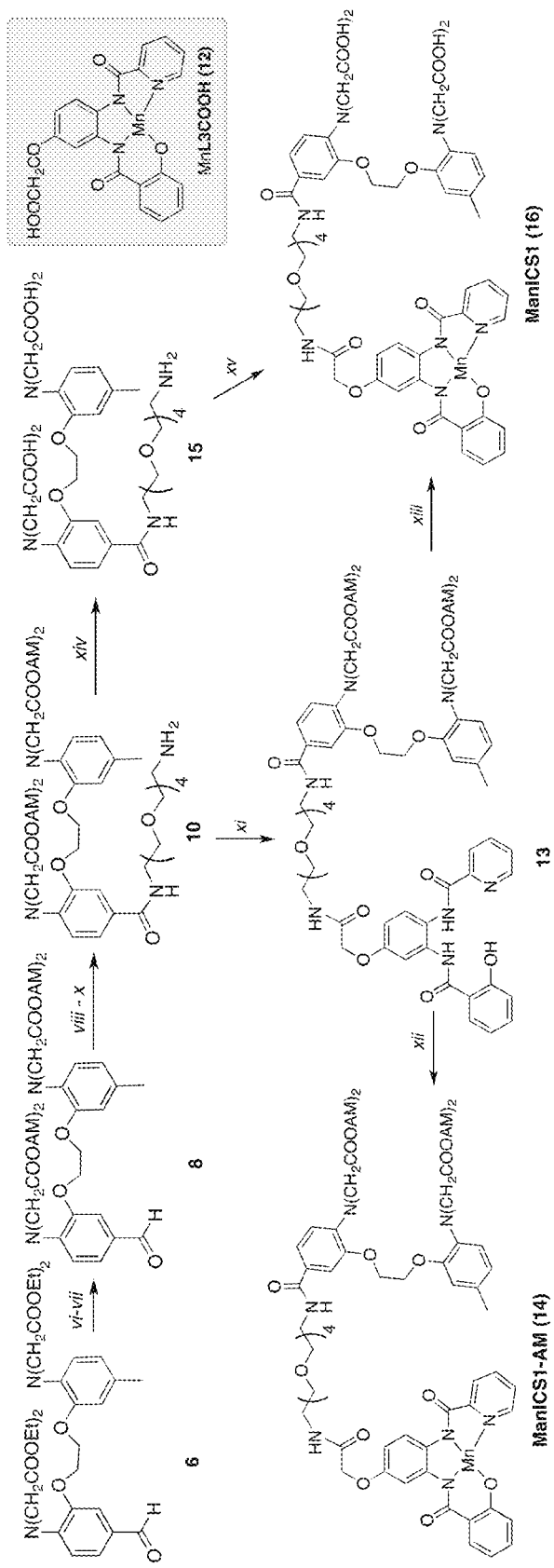
FIG. 2 depicts a synthesis of ManICS1 and ManICS1-AM [The following conditions are noted: vi) NaOH (96%); vii) 7, $AcOCH_2Br$, N,N-diisopropylethylamine (DIEA) (67%); viii) $NaH_2PO_4$, $NaClO_2$ (95%); ix) 9, (benzotriazol-1-yl-oxytripyrrolidinophosphonium hexafluorophosphate) (PyBOP), DIEA, $NH_2$—$CH_2(CH_2OCH_2)_4$ $CH_2$—NH(tert-butyloxycarbonyl) ($NH_2$-$PEG_4$-NHBoc) (55%); x) trifluoroacetic acid (TFA), dichloromethane (DCM) (98%); xi) $L_3$COOH (12 without Mn), PyBOP, DIEA (54%); xii) manganese (III) acetate $Mn(OAc)_3.2(H_2O)$ (85%); xiii) 10% (v/v) cell lysate, (3-(N-morpholino)propanesulfonic acid) (MOPS) (25 mM, pH 8); xiv) KOH (6 eq), $H_2O$ (89%); xv) $MnL_3COOH$, PyBOP, DIEA (38%)].

Certain ions (e.g., calcium, potassium, sodium) are important for signal transduction in cells, where they help coordinate biological processes ranging from embryonic development to neural function in the brain. Accordingly, in some embodiments, sensors and related methods described herein may be used to detect such ions and other analytes to gain a functional and/or physiological understanding of the biology of major disease areas, e.g., in neuroscience, which may lead to the discovery of addressable functional mechanisms in health and disease.

In some embodiments, sensors and related methods provided herein facilitate drug development by providing new tools for pharmacological screening and characterization. In some embodiments, using the ion response (e.g., calcium signaling as a readout facilitates the study of drug or physiological effects.

In some embodiments, sensors and related methods provided herein may be used for clinical diagnostic imaging. In some embodiments, sensors may be used, for example, to visualize cell signaling for diagnosis in numerous conditions, including neurological and muscular disorders, as well as immunological and endocrine conditions and others.

Sensors

In some embodiments, sensors provided herein comprise the structure Y-L-Z, wherein: Y is an analyte binding moiety; Z is a lipophilic, branched chelating moiety; and L is a linker that covalently links Y and Z. Accordingly, in some embodiments, the sensor comprises an organic or an organometallic compound. In some embodiments, the sensor further comprises an additional Y, Z, L, -L-Y, or -L-Z covalently bound to Y or Z. In some embodiments, the sensor further comprises an additional L-Z covalently bound to Y (e.g., Z-L-Y-L-Z). In some embodiments, the sensor further comprises an additional -L-Y covalently bound to Z (e.g., Y-L-Z-L-Y).

Various analytes that may be detected using the sensors described herein include metal ions, nitric oxide, or other species associated with normal biological function. The analyte may be present within a subject (e.g., a human), and, in some cases, may be present within a cell. In some cases, the analyte may be present within a subject in a location exterior to a cell. In some cases, the analyte is a metal ion, such as a toxic metal ion. Examples of metal ions include, but are not limited to, $Zn^{2+}$, $Ca^{2+}$, $Hg^{2+}$, $Cd^{2+}$, $Pb^{2+}$, $Na^+$, $Mg^{2+}$, $Mn^{2+}$, $Fe^{2+}$, $Co^{2+}$, $Ni^{2+}$, and $Cu^{2+}$. In some cases, the analyte is $Zn^{2+}$, $Ca^{2+}$, $Mg^{2+}$, $Hg^{2+}$, $Cd^{2+}$, or $Pb^{2+}$. In some embodiments, the analyte may be a zinc ion or calcium ion. In certain embodiments, the analyte may be a magnesium ion.

In some embodiments, the analyte may be a calcium ion. Calcium is a component of cellular signaling systems and participates in brain function among other processes. Muscles (including the heart) may also depend on regulation of calcium, and calcium has been implicated in myocardial dysfunction. In one embodiment, a sensor may be useful in the determination of calcium ions within a cell, such as a muscle cell or neuronal cell.

In some embodiments, the analyte binding moiety contains at least one aromatic group. In some embodiments, contains at least one aromatic group selected from the group consisting of monocyclic aryl (e.g., phenyl), bicyclic aryl (e.g., naphthyl), monocyclic heteroaryl (e.g., pyridyl, pyrimidyl, pyrrolyl, imidazolyl), and bicyclic heteroaryl (e.g., quinolyl, indolyl).

In certain embodiments, the analyte binding moiety is a polyaminocarboxylate chelator. In certain embodiments, the analyte binding moiety is a polyaminocarboxylate chelator selected from the group consisting of polyaminocarboxylate chelator is selected from the group consisting of ethylenediaminetetraacetic acid (EDTA), ethylene glycol-bis(β-aminoethyl ether N,N,N',N'-tetraacetic acid (EGTA), diethylenetriaminepentaacetic acid (DTPA), 2-[(2-amino-5-methylphenoxy)methyl]-6-methoxy-8-aminoquinoline-N, N,N',N'-tetraacetic acid (quin-2), 1-(2-nitro-4,5-dimethoxyphenyl)-1,2-diaminoethane-N,N,N',N'-tetraacetic acid (DM-nitrophen), and o-aminophenol-N,N,O-triacetic acid (APTRA). In some embodiments, the analyte binding moiety selectively chelates metal ions. In some embodiments, the analyte binding moiety is ethylenediaminetetraacetic acid (EDTA). In certain embodiments, the analyte binding moiety is ethylene glycol-bis(β-aminoethyl ether) N,N,N',N'-tetraacetic acid (EGTA). In certain embodiments, the analyte binding moiety is a metal ion-selective crown ether.

In some embodiments, an analyte binding moiety comprises a selective metal ion chelating moiety. In some embodiments, the selective metal ion chelating moiety is cell permeable. In some embodiments, the selective metal ion chelating moiety comprises a selective calcium chelating moiety derived from 1,2-bis(2-aminophenoxy)ethane-N,N,N',N'-tetraacetic acid (BAPTA). In some embodiments, BAPTA, which is highly polar and membrane-impermeant in its $Ca^{2+}$-binding acidic form, may be modified with modifying groups (e.g., with acetomethoxy (AM) ester groups) to produce a neutral, inactive complex that is readily internalized inside cells. In certain embodiments, the selective calcium chelating moiety derived from BAPTA does not comprise carboxyl moieties. In certain embodiments, in the selective calcium chelating moiety derived from BAPTA, each of the moieties —C(=O)OH of BAPTA is replaced with the moiety —C(=O)OR, wherein each instance of R is independently substituted or unsubstituted $C_{1-6}$ alkyl. In certain embodiments, each instance of R is $C_{1-6}$ alkyl or $C_{3-10}$ cycloalkyl, wherein R is unsubstituted or substituted with —$OR^1$, —C(=O)$R^1$, —O—C(=O)$R^1$, —C(=O)$OR^1$, —$NR^1$—C(=O)$R^1$, or —C(=O)N($R^1$)$_2$ wherein each $R^1$ is independently H, substituted or unsubstituted $C_{1-6}$ alkyl (e.g., methyl, ethyl, propyl, butyl), or substituted or unsubstituted $C_{3-10}$ cycloalkyl (e.g., cyclopentyl, cyclobutyl, cyclopentyl, cyclohexyl). In certain embodiments, each instance of R is —$CH_2$—O—C(=O)—$CH_3$. In some embodiments, after internalization, the modifying groups (e.g., AM esters) undergo hydrolysis (e.g., catalyzed by intracellular esterases). In some embodiments, this process may activate the sensor (also referred to herein as an indicator) and trap it in the cell cytosol, where it functions as a cytosolic [$Ca^{2+}$] imaging agent.

In some embodiments, the lipophilic, branched chelating moiety is capable of binding a metal ion, such as a paramagnetic metal ion (e.g., $Mn^{3+}$, $Fe^{3+}$). In some embodiments, the analyte binding moiety is capable of binding an analyte such that an MRI and/or optical property of the sensor is shifted upon binding the analyte. As described herein, the presence or absence of a metal ion bound to the chelating moiety (chelator group), or, the type of metal ion bound to the chelating moiety, may affect one or more properties of the sensor, such as an MRI or optical property. In some cases, the sensor comprises a chelating moiety which binds a paramagnetic metal ion, such that the sensor exhibits an MRI signal upon exposure to MRI conditions, e.g., exposure to a magnetic field. In some cases, the sensor comprises a chelating moiety which does not bind a metal ion or binds a diamagnetic metal ion, such that the sensor exhibits a luminescence emission or absorption upon exposure to electromagnetic radiation.

As used herein, the term "paramagnetic metal ion" refers to a metal ion having unpaired electrons, causing the metal ion to have a measurable magnetic moment in the presence of an externally applied field. Examples of suitable paramagnetic metal ions, include, but are not limited to, ions of iron, nickel, manganese, copper, gadolinium, dysprosium, europium, and the like. $Mn^{2+}$, $Mn^{3+}$, $Fe^{2+}$, and $Fe^{3+}$ are non-limiting examples of paramagnetic metal ions. In some embodiments, a sensor or composition of the disclosure comprises a chelator group bound to a paramagnetic metal ion, wherein the paramagnetic ion is an ion of iron or manganese.

In certain embodiments, the lipophilic, branched chelating moiety comprises an aromatic group. In some embodiments, the lipophilic, branched chelating moiety comprises one or more cyclic moieties. In some embodiments, the lipophilic, branched chelating moiety is independently selected from the group consisting of optionally substituted monocyclic carbocyclyl (e.g., cyclopentyl, cyclohexyl), optionally substituted bicyclic carbocyclyl (e.g., decahydronaphtalenyl, bicyclo[2.2.1]heptanyl), optionally substituted monocyclic heterocyclyl (e.g., tetrahydrofuranyl, tetrahydropyranyl, pyrrolidinyl, pyrolinyl), and optionally substituted bicyclic heterocyclyl (e.g., decahydroquinolinyl). In some embodiments, the lipophilic, branched chelating moiety is independently selected from the group consisting of optionally substituted monocyclic aryl (e.g., phenyl, anilinyl), optionally substituted bicyclic aryl (e.g., naphthyl), optionally substituted monocyclic heteroaryl (e.g., pyridyl, pyrimidyl, pyrrolyl, imidazolyl), and optionally substituted bicyclic heteroaryl (e.g., quinolyl, indolyl). In certain embodiments, the lipophilic, branched chelating moiety comprises aromatic fluorophore.

In some embodiments, the lipophilic, branched chelating moiety comprises a planar lipophilic ligand (e.g., a planar cell-permeable aromatic fluorophore). In some embodiments, the planar lipophilic ligand belongs to a family of planar phenylenediamido (PDA)-based $Mn^{3+}$ complexes (see, e.g., FIG. 1A, top right box) that act as $T_1$ MRI contrast agents and can undergo cell internalization and trapping analogous to organic AM ester-derivatized fluorophores. Conjugation of such a complex to the selective metal ion chelating moiety (e.g., BAPTA-based chelator) may result in a candidate MRI metal ion (e.g., calcium ion) sensor with similar physicochemical properties to optical imaging dyes like Fluo-4 (PubChem CID: 25058176), Fura-2 (PubChem. CID: 57054), and Oregon Green BAPTA (PubChem. CID: 102028682). In some embodiments, such a probe could be administered to cells in modified form with modifying groups (e.g., AM ester), which probe (also referred to herein as a sensor) would be internalized into a cell and activated (see, e.g., FIG. 1A).

In some embodiments, interactions between the selective metal ion chelating moiety (e.g., based on BAPTA) and the planar lipophilic ligand (e.g., an Mn-PDA) of the activated sensor provide a basis for transducing calcium concentration changes into $T_1$-weighted MRI signals. Accordingly, in embodiments provided herein, magnetic resonance imaging (MRI) provides for wide-field deep-tissue ion imaging (e.g., calcium imaging) in animals and humans. MRI achieves a combination of unlimited depth penetration, relatively high 3D spatial resolution (<100 μm in some contexts), and sensitivity to a wide variety contrast mechanisms. In some embodiments, the sensors described herein are used for real-time functional magnetic resonance imaging of a signaling ion (e.g., calcium, for calcium ion signaling) in cells and tissues.

In some embodiments, L, is an unbranched $C_{4-40}$ alkylene, unbranched $C_{4-40}$ alkenylene, or unbranched $C_{4-40}$ alkynylene. In certain embodiments, 0, 1, or more methylene units of the unbranched $C_{4-40}$ alkylene, unbranched $C_{4-40}$ alkenylene, or unbranched $C_{4-40}$ alkynylene are independently replaced with O, N, N($R^F$), C(=O)O, C(=O)$NR^F$, S, optionally substituted carbocyclyl, optionally substituted heterocyclyl, optionally substituted aryl, or optionally substituted heteroaryl as valency permits. In certain embodiments, 1 or more methylene units of the unbranched $C_{4-40}$ alkylene is N (e.g., —$CH_2CH_2C$=$NCH_2$—). In certain embodiments, 1 or more methylene units of the unbranched $C_{4-40}$ alkylene is C(=O)O. In certain embodiments, 1 or more methylene units of the unbranched $C_{4-40}$ alkylene is C(=O)$NR^F$. In certain embodiments, 1 or more methylene units of the unbranched $C_{4-40}$ alkylene is optionally substituted carbocyclyl (e.g., cyclopentyl, cyclobutyl, cyclopentyl, cyclohexyl). In certain embodiments, 1 or more methylene units of the unbranched $C_{4-40}$ alkylene is optionally substituted heterocyclyl (e.g., tetrahydrofuranyl, tetrahydropyranyl, pyrrolidinyl, pyrolinyl, dioxopyrrolidinyl) In certain embodiments, 1 or more methylene units of the unbranched $C_{4-40}$ alkylene is optionally substituted aryl (e.g., phenyl

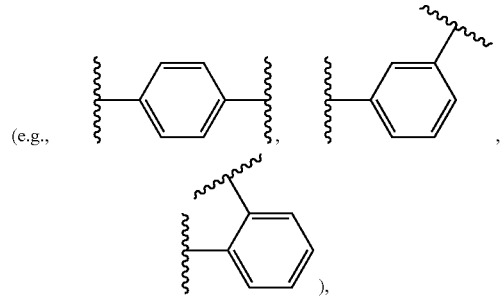

(e.g., anilinyl

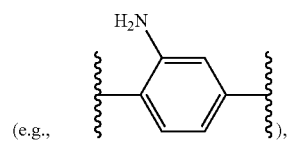 [SMILES: *c1ccc(*)c(N)c1]

(e.g., ),

In certain embodiments, 1 or more methylene units of the unbranched $C_{4-40}$ alkylene is optionally substituted heteroaryl (e.g., pyridyl, pyrimidyl, pyrrolyl, imidazolyl, tetrazolyl, triazolyl, quinolyl, indolyl). In certain embodiments, $R^F$ is H. In some embodiments, $R^F$ is unsubstituted $C_{1-6}$ alkyl (e.g., methyl, ethyl, propyl, isopropyl, butyl, pentyl, hexyl). In certain embodiments, a methylene unit is independently substituted with oxo. In certain embodiments, a methylene unit is independently substituted with —$OR^a$ (—$OCH_3$ or —$OCH_2CH_3$). In some embodiments, a methylene unit is substituted with halogen (e.g., —F, —Cl, —Br, or —I. In certain embodiments, a methylene unit is substituted with $C_{1-6}$ alkyl (e.g., methyl, ethyl, propyl, isopropyl, butyl, pentyl). In certain embodiments, a methylene unit is substituted with $C_{1-6}$ alkyl substituted with one or more instances of halogen (e.g. —$CF_3$, —$CHF_2$, —$CH_2F$, —$CH_2CF_3$).

Figure 6:
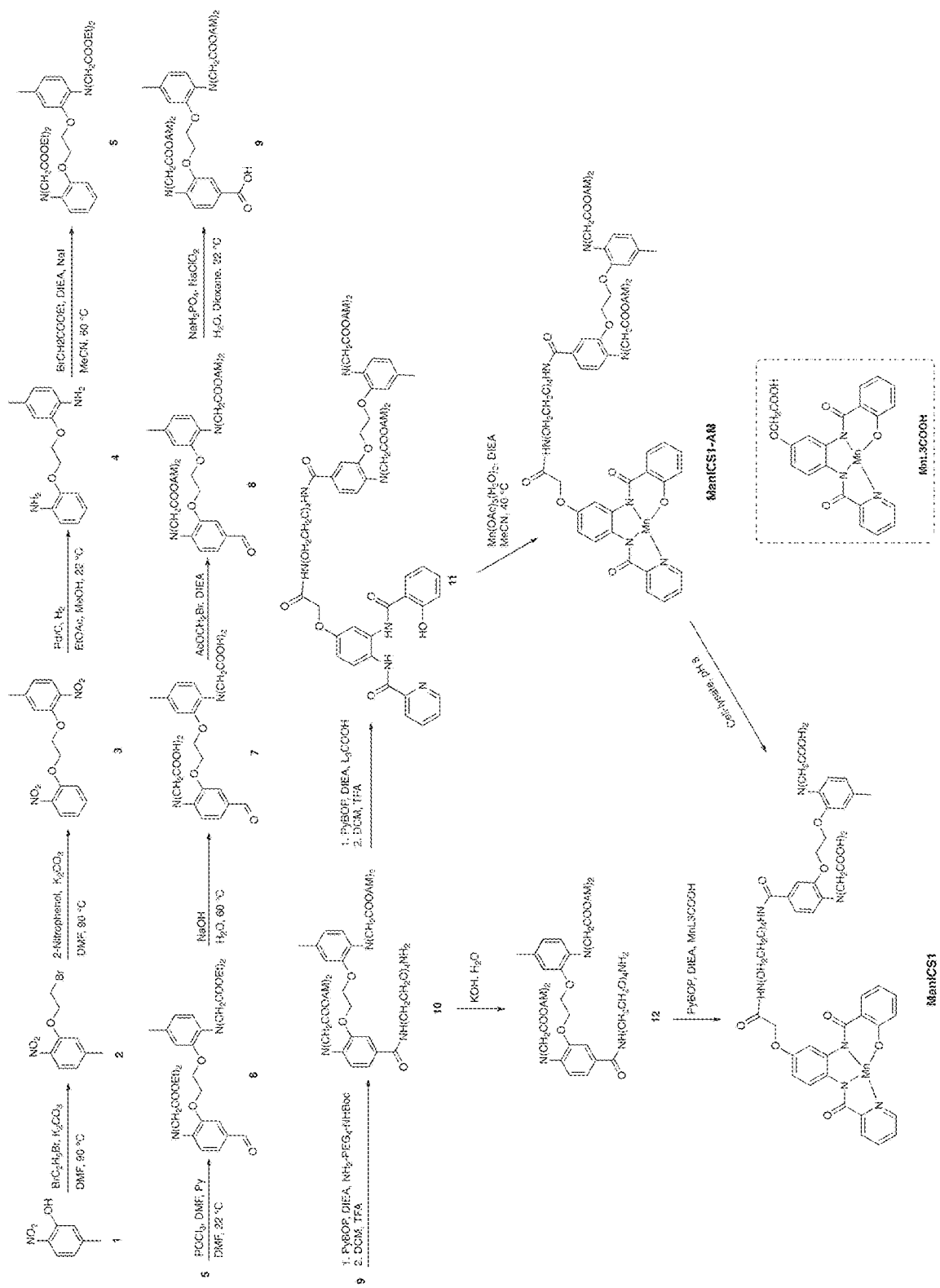
FIG. 6 depicts a synthesis of ManICS1 and ManICS1-AM.

In some embodiments, methods of making a sensor are provided (See, e.g., Examples and FIG. 6).

In some embodiments, methods of using the sensor are provided. In some embodiments, the sensor is used to monitor changes in intracellular metal ion (e.g., calcium ion) levels by MRI (e.g., proton MRI).

Chemical Definitions

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"), in some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted ("unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$,

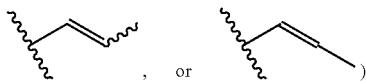
, or )

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$) octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$alkynyl"). Unless otherwise specified, each instance of a heteroalkynyl group is independently unsubstituted (an "unsubstituted heteroalkynyl.") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more cathocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1,2, or 3 atoms in the heterocyclic ring system are independently oxygen, nitrogen, or sulfur, as valency permits.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 rings heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolindinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2indolyl) or the rims that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl and phenazinyl.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O) R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O) NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC (=O)SR$^{aa}$, —SC(=O)OR$^{aa}$, —SC(=O)R$^{aa}$, —P(=O)$_2$ R$^{aa}$, —OP(=O)$_2$R$^{aa}$, —P(=O)R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N (R$^{bb}$)$_2$, —P(=O)(NR$^{bb}$)$_2$, —OP(=O)(NR$^{bb}$)$_2$, —NR$^{bb}$P (=O)(OR$^{cc}$)$_2$, —NR$^{bb}$P(=O)(NR$^{bb}$)$_2$, —P(R$^{cc}$)$_2$, —P (R$^{cc}$)$_3$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C (=O)R$^{aa}$, =NNR$^{bb}$C(=O)OR$^{aa}$, =NNR$^{bb}$S(=O)$_2$ R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ to perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ee}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —C(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$C$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —PP(=O)(C$_{1-6}$ alkyl)$_2$, —OP(=O)(OC$_{1-6}$ alkyl)$_2$, C$_{1-6}$ alkyl, perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$_{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted C$_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, the carbon atom substituents are independently halogen, substituted (e.g., substituted with one or more halogen) or unsubstituted C$_{1-6}$ alkyl, —OR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted C$_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted C$_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group (e.g., Bn, Boc, Cbz, Fmoc, trifluoroacetyl, triphenylmethyl, acetyl, or Ts).

In certain embodiments, the molecular weight of a carbon atom substituent is lower than 250, lower than 200, lower than 150, lower than 100, or lower than 50 g/mol. In certain embodiments, a carbon atom substituent consists of carbon, hydrogen, fluorine, chlorine, bromine, iodine, oxygen, sulfur, nitrogen, and/or silicon atoms. In certain embodiments, a carbon atom substituent consists of carbon, hydrogen, fluorine, chlorine, bromine, iodine, oxygen, sulfur, and/or nitrogen atoms. In certain embodiments, a carbon atom substituent consists of carbon, hydrogen, fluorine, chlorine, bromine, and/or iodine atoms. In certain embodiments, a carbon atom substituent consists of carbon, hydrogen, fluorine, and/or chlorine atoms.

The term "halo" or "halogen" refers to fluorine (fluoro, —F), chlorine (chloro, —Cl), bromine (bromo, —Br), or iodine (iodo, —I).

The term "oxo" refers to the moiety ═O.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

EXAMPLES

Example 1

Sensing Intracellular Calcium Ions Using a Manganese-Based MRI Contrast Agent Building Block for Intracellular MRI Calcium Sensors To examine the potential of Mn-PDA contrast agents to function as building blocks for the sensor design of FIG. 1A, MRI measurements were performed to assess the potential of BAPTA to interact with three paramagnetic chelates (FIG. 1A, inset). Addition of 1.1 equivalents of BAPTA to two of the Mn-PDA complexes, MnL1 and MnL3, produced significant effects on the $T_1$-weighted MRI contrast induced by these compounds in buffer. These BAPTA-dependent contrast changes were reversed by addition of equimolar $Ca^{2+}$ (FIG. 1B). This was consistent with Mn-PDA moieties competing with $Ca^{2+}$ for binding to BAPTA molecules. The changes were quantified in terms of $T_1$ relaxivity ($r_1$) values, which were defined as the slope of the $T_1$ relaxation rate ($1/T_1=R_1$) vs. concentration of each paramagnetic complex. Calcium-dependent changes in $r_1$ observed for MnL1 and MnL3 in the presence of BAPTA were 105% and 23%, respectively; both were significant.

Mixtures of MnL1 and MnL3 with BAPTA both showed calcium-dependent MRI properties. The spectroscopic behavior of MnL1 and MnL3 in the presence of BAPTA over time was examined, and it was found that the MnL1-containing mixture displayed sharp changes indicative of degradation, while the MnL3 mixture remained unperturbed and apparently stable (FIG. 1D). These results were confirmed by high resolution mass spectrometry of the two mixtures. Even after 24 hours, the MnL3 mixture with BAPTA displayed a prominent base peak associated with [MnL3+Cl]$^-$ (m/z=419.77) but no peak for demetallated L3 (FIG. 1D). In contrast, the MnL1 mixture with BAPTA developed a strong peak for uncomplexed L1 (m/z=347.37), indicating dissociation of the MnL1 complex. These results indicated that MnL3 and BAPTA constituted a suitable pair of building blocks for intracellular calcium sensor construction.

Synthesis and Characterization of ManICS1 and ManICS1-AM

To form a first manganese-based intracellular calcium sensor (ManICS1) from MnL3 and BAPTA, ManICS1 and its AM ester derivative ManICS1-AM were synthesized using a series of multistep reactions starting from 5-methyl-2-nitrophenol (1) (FIG. 6). Synthesis of compound 7 as the parent BAPTA derivative for preparing ManICS was adapted from the procedure reported. by Grynkiewicz et al. (Grynkiewicz G; Poenie M; and Tsien R Y. J. Biolog. Chem. 1985, 260, 3440-3450). Conversion of the aldehyde group of this compound to a carboxylic acid was performed through Pinick oxidation, which resulted in high yields without using transition metal catalysis. Successive attachment of a polyethylene glycol linker and carboxylate-modified L3 derivative to compound 7 were achieved using benzotriazol-1-yl-oxytripyrrolidinophosphonium hexafluorophosphate, which produced higher yields than other coupling reagents. The resulting compound 11 was metallated to form ManICS1-AM by reaction with Mn(OAc)$_3$.2(H$_2$O) in acetonitrile in the presence of N,N-diisopropylethylamine. Enzymatic hydrolysis of ManICS1-AM or direct coupling of compound 12 to MnL3COOH afforded ManICS1 in moderate yields (FIG. 6).

The calcium responsiveness of ManICS 1 was measured in buffer by titrating the compound with calcium chloride over a concentration range relevant to intracellular signaling. Images indicated clear enhancement of $T_1$-weighted MRI intensity as calcium ions were added. (FIG. 3A). No image changes were observed when $Mg^{2+}$ was added in place of $Ca^{2+}$, indicating specificity of the responses to calcium. Apparent relaxivity values were determined for each condition (FIG. 3B). The data indicated that calcium binding induced a 34% increase in relaxivity of ManICS1, with $r_1$ values ranging from 3.8 $mM^{-1}s^{-1}$ to 5.1 $mM^{-1}s^{-1}$ over the full. calcium range. As expected, no significant $r_1$ change was observed with $Mg^{2+}$ titration. The dissociation constant for calcium binding to ManICS1 was determined to be 18 micromolar (μM). This value is higher than most high affinity fluorescent indicators used for intracellular $Ca^{2+}$ imaging, but is still sufficient for transducing [$Ca^{2+}$] fluctuations by as little as 1 micromolar (μM) from baseline into $T_1$-weighted image changes of ~1% or higher, equivalent to signals commonly detected in functional MRI experiments.

To probe the mechanism of calcium sensing by ManICS1, a series of experiments were performed. The apparent calcium affinity of the probe was relatively low for the BAPTA derivative that was used, which in the context of fluorescent sensors generally confers calcium binding with submicromolar calcium $K_d$ values. To further evaluate calcium sensing, a manganese-free ManICS1 analog was formed and its calcium affinity was measured by titration with a spectroscopic readout. A separate calcium titration series was also performed with three different concentrations of ManICS1. Data from the three datasets produced $K_d$ estimates that did not differ significantly from one another.

To demonstrate that the ester groups of ManICS1-AM are capable of undergoing cleavage in the cytosolic milieu, the compound was incubated in clarified cell lysate (10% by volume) and the high performance liquid chromatography (HPLC) time course was compared to that of ManICS1 and ManICS1-AM incubated in buffer alone. It was found that five hours of exposure to cell lysate was sufficient to result in complete conversion of the ManICS1-AM HPLC peak into a product that eluted at the same time as ManICS1 (FIG. 3C). The identity of this product as ManICS1 was confirmed by mass spectrometry, indicating that all four esters of ManICS1-AM were released within the incubation time. As a further test of the behavior of ManICS1 ester derivatives, ManICS1-Et was synthesized, in which all four BAPTA carboxylates were modified by ethyl esters rather than AM groups. HPLC data indicated that ManICS1-Et incubation did not yield ManICS1 after five hour incubation with lysate. Thus, in some embodiments, genetically-targeted cleavage may be useful to bring about intracellular accumulation of ManICS-Et, in which appropriately selective esterases are expressed ectopically.

ManICS1-AM Labeled Cells and Enabled Intracellular Calcium-Sensitive MRI

Figure 4A:
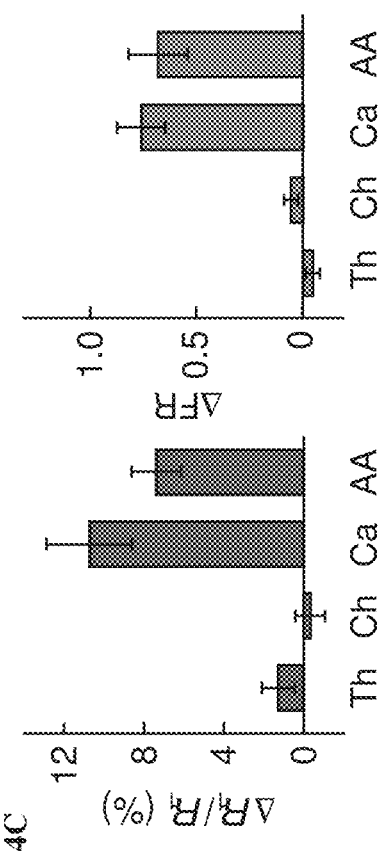
FIGS. 4A to 4D show that ManICS1 reported calcium-dependent MRI signal changes in cells.
Figure 4C:
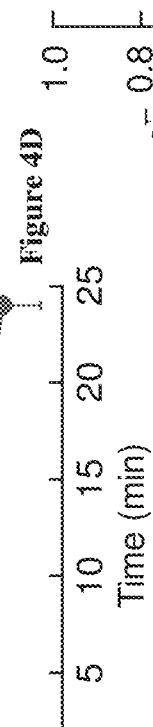
Figure 4B:
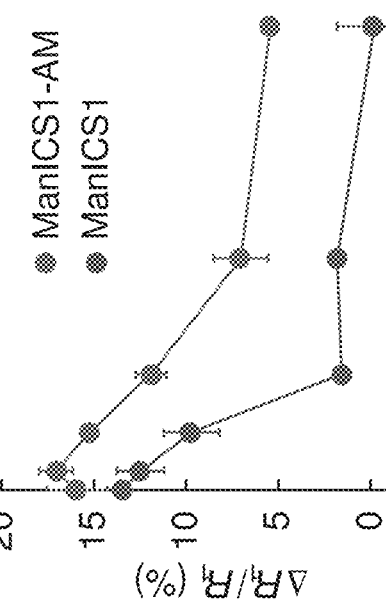

To validate the potential for ManICS1-AM to enable readouts of intracellular calcium by $T_1$-weighted MRI, the ability of ManICS1-AM to label cells and subsequently be retained was first examined. Cultured HEK293 cells were incubated with ManICS1-AM or ManICS1 followed by washing and then MRI analysis. It was found that cells incubated with the two agents underwent a comparable increase in R, compared with control cells (FIG. 4A), suggesting that both agents were internalized to some extent. When a delay was inserted, followed by additional washing, between the labeling period and the MRI, it was found that ManICS1-treated cells returned quickly to baseline values within 5 hours, while cells treated with ManICS1-AM maintained elevated contrast for up to 24 hours. To assess the subcellular localization of manganese following ManICS1-AM or ManICS labeling, cells were fractionated into cytosolic, organellar, and membranous compartments and the samples were analyzed by inductively coupled plasma optical emission spectroscopy (ICP-OES). The ICP-OES results indicated that ManICS1-AM labeling produced long-lasting cytosolic elevations in manganese content, while ManICS labeling produced shorter-lived organellar accumulation. These results were consistent with the hypothesis that ManICS1-AM penetrates cells and undergoes cytosolic accumulation as diagrammed in FIG. 1A, while ManICS1 in its acidic form may be internalized to some extent via endocytosis.

To assess the potential for internalized ManICS1 to transduce cytosolic calcium concentrations into $R_1$ changes detectable by MRI, cultured HEK293 cells were labeled again with ManICS1-AM and then challenged with stimuli known to elevate intracellular $[Ca^{2+}]$. Cells treated with thapsigargin and carbachol did not show elevated $R_1$, whereas addition of calcimycin or arachidonic acid produced substantial increases in mean $R_1$. The same four stimulants were applied separately to cells prelabeled with the fluorescent calcium indicator derivative Fura-2-AM. Fluorescence ratio measurements from these cells closely paralleled the results obtained by MRI analysis of ManICS1-AM-labeled cells, indicating that the variable MRI results were indicative of actual intracellular calcium responses.

Figure 4D:
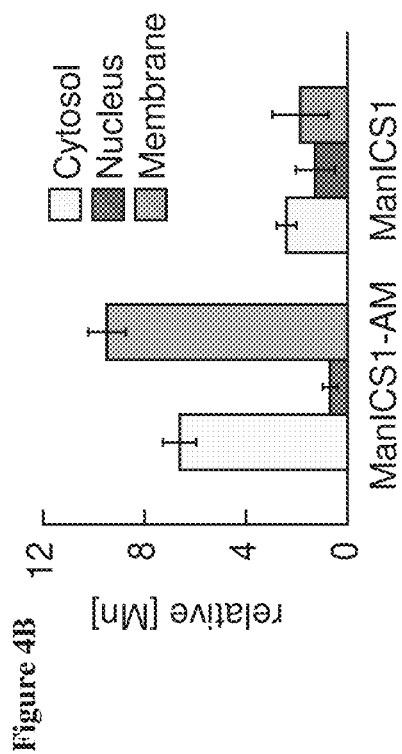
Figure 5:
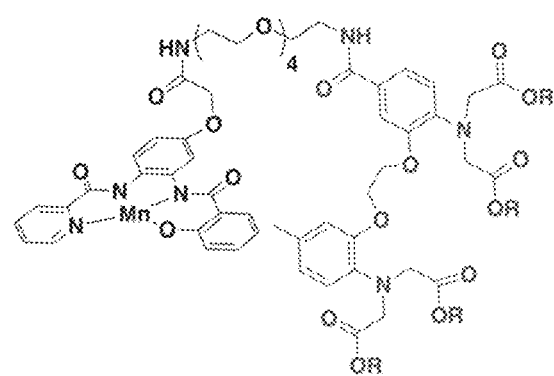
FIG. 5 shows molecular structures of intracellular calcium sensors for MRI. AM is acetoxymethyl.

As a further test of the calcium-dependent contrast properties conferred by ManICS1-AM, intracellular calcium levels were titrated and the profile of resulting $R_1$ changes was examined. Intracellular calcium levels were regulated by controlling extracellular calcium using a standard buffering system in the presence of the ionophore calcimycin, which equilibrates calcium levels across the cell membrane. Results demonstrated progressive changes in $R_1$ as $[Ca^{2+}]$ ranged from 1 micromolar (μM) to 100 micromolar (μM), establishing a midpoint ($EC_{50}$) for intracellular calcium sensing by ManICS1 of about 5 micromolar (μM) (FIG. 4D). As a further experiment, cells in high calcium conditions were treated, washed, and then returned to low calcium conditions before MRI was performed. Cells treated in this way displayed the lower $T_1$-weighted MRI signal characteristic of low $[Ca^{2+}]$ conditions, indicating that elevated calcium did not produce irreversible increases in $R_1$.

These results showed MRI-based measurement of intracellular calcium using a manganese-based MRI contrast agent that parallelled properties of fluorescent probes for cytosolic $Ca^{2+}$ imaging. In this work, ManICS1 was synthesized, which incorporated membrane-permeable building blocks and involved the AM ester-based approach for cell labeling and intracellular trapping of the probe. ManICS1 reported calcium levels analogously to the widely used optical calcium sensor Fura-2. The novel probe may be used for MRI-based spatiotemporal mapping of calcium signaling processes in contexts where optical imaging approaches have previously been successful.

Example 2

Methods and Materials

Magnetic Resonance Imaging

Most MRI data were acquired on a 7 T Bruker Biospec0 system using a $T_1$-weighted 2D gradient echo sequence (echo time, TE=5 ms, repetition time, TR=100 ms; flip angle, FA=65 degrees (°)). Longitudinal relaxivity ($r_1$) measurements were acquired using a 2D spin echo sequence (TE=11 ms, TR=125, 200, 400, 800, 1500, 3000, and 5000 ms), with in-plane resolution of 200×200 microns squared ((μm)$^2$) and 2 mm slice thickness. $R_1$ maps and values were generated using an MRI Analysis Calculator Plugin for ImageJ (National Institutes of Health, Bethesda, Md.) or Matlab scripts (Mathworks, Natick, Mass.). Stimulus-dependent $R_1$ changes in cells were calculated as $\Delta R_1/R_1=[R_1$(incubated cells)$-R_1$(naive cells)$]/R_1$(naive cells). Statistical comparisons between paired conditions were performed using Student's t-test, and all error bars denote the standard error of the mean from multiple measurements, unless otherwise noted.

In Vitro Characterization of ManICS1 and ManICS1-AM

ManICS1, calcium, and magnesium stock solutions were all prepared in 25 mM 3-(N-morpholino)propanesulfonic acid (MOPS), pH 7.4, with 100 mM KCl. Titration series were prepared as separate triplicates for each data point in the presence of constant concentrations of ManICS1, confirmed subsequently by ICP-OES analysis. Samples were arrayed into microtiter plates and measured by MRI using a Bruker (Billerica, Mass.) Avance 7 T scanner. Unused wells were filled with buffer, and imaging was performed on a 2 mm slice through the sample. Calcium affinity of manganese-free ManICS1 was determined using optical spectroscopy.

Cell Labeling with ManICS1-AM

HEK293 cells (Freestyle 293-F, Thermo Fischer Scientific, Waltham, Mass.) were cultured and prepared for relaxometry. To assess uptake, cells were exposed to contrast agents in media for 30 min, washed with Hank's buffered saline solution (HBSS), and then immediately pelleted by centrifugation at 750 g for imaging, incubated in media again for varying time intervals, or stimulated with pharmacological agents. Subcellular fractionation analysis of ManICS1-AM-labeled cells was conducted. Cells were incubated with agent for 30 min, washed in HBSS and permeablized on ice with saponin to collect cytosolic fractions for analysis with ICP-OES.

Measurement of Intracellular Calcium Responses

For stimulation experiments, cells were incubated with 10 micromolar (μM) ManICS1-AM for 2 h for labeling and AM ester cleavage. Pharmacological stimulation was conducted by adding 10 micromolar (μM) thapsigargin, 5 micromolar (μM) charbocol, 5 micromolar (μM) calcimycin, or 10 micromolar (μM) arachidonic acid (Sigma-Aldrich, St. Louis, Mo.). To test reversibility of the calcium response, cells were prepared with ManICS1-AM and 5 micromolar (μM) calcimycin maintained for the duration of the experiment, washed in calcium free media, divided into two aliquots to be washed again or returned to 2 mM $Ca^{2+}$. For the titration curve cells were maintained in 5 micromolar (μM) calcimycin first in 100× volume calcium-free buffer, then while incubated in 100× volume media with 0-1 mM calcium for 1.5 min at 37 degrees Celsius (° C.).

For comparison stimulation measurements performed with Fura-2, adherent HEK293 cells were seeded onto a 96 well plate at 5,000 cells/well and grown for two days until 90% confluent. Cells were then incubated for 45 min in 10 micromolar (μM) Fura-2 and then washed with media. Stimulants (10 micromolar (μM) thapsigargin, 5 micromolar charbocol, 5 micromolar (μM) calcimycin, or 10 micromolar (μM) arachidonic acid) were quickly added to multiple wells via multipipettor and fluorescence output was measured using a plate reader. Measurements were repeated every 5 minutes for 40 minutes to chart the time course of calcium concentration changes at room temperature.

Example 3

ManICS1-AM Labels Cells and Enables Intracellular Calcium-Sensitive MRI

To test the ability of ManICS1-AM to enable readouts of intracellular calcium by $T_1$-weighted MRI, its propensity was first examined to accumulate within cells. Cultured HEK293 cells were incubated with 10 μM ManICS1-AM or ManICS1 for 30 minutes, followed by washing and MRI analysis (FIG. 7A). It was found that cells incubated with the cell permeable ManICS1-AM underwent a substantial increase in $R_1$ that persisted above basal levels for up to 24 h, while cells labeled with ManICS1 experienced a somewhat lesser increase in $R_1$ that returned to baseline within 5 h. To assess the subcellular localization of manganese following ManICS1-AM or ManICS1 labeling, cytosolic fractions were isolated from cell lysates and the samples were analyzed by inductively coupled plasma mass spectrometry (ICP-MS). The ICP-MS results indicated that only ManICS1-AM labeling produced cytosolic elevations in manganese content (FIG. 7A inset). These results are consistent with the hypothesis that ManICS1-AM penetrates cells and is retained in the cytosol (FIG. 1A).

To assess the potential for internalized ManICS1 to report stimulus-induced cytosolic calcium concentrations as changes detectable by MRI, HEK293 cells were again labeled with ManICS1-AM; then the cells were challenged with pharmacological agents that elevate cytosolic calcium levels (FIG. 7C). Calcimycin and arachidonic acid both produced 8-10% increases in mean $R_1$ values recorded within 20 min of stimulation. Cells treated with thapsigargin or carbachol, which are thought to cause only short-lived $Ca^{2+}$ responses, did not show an elevated $R_1$. Control measurements using the fluorescent calcium indicator derivative Fura-2FF-AM collected using similar stimulus conditions closely paralleled the results obtained by MRI of ManICS1-AM-labeled cells (FIG. 7D), showing that the MRI results provide an accurate measure of intracellular calcium perturbations.

To examine the reversibility and dynamics of ManICS1-based calcium sensing the optogenetic $Ca^{2+}$ actuator BACCS2 was used to stimulate contrast agent-labeled cells while performing functional imaging with MRI. In preparation for these experiments, cells were embedded in a gel matrix that permitted effective $Ca^{2+}$ exchange at high cell density. BACCS2-expressing cells loaded with ManICS1-AM showed dynamic light-dependent image changes averaging 0.8±0.2% in amplitude (FIG. 7E), matching a time course obtained using optical measurements of cells loaded with the fluorescent calcium indicator X-Rhod-1 (FIG. 7F). Stimulation of ManICS1-AM-labeled cells that did not express BACCS2 or MnL3-labeled cells expressing BACCS2 produced negligible MRI effects. Both were significantly lower than those observed with ManICS1-AM in BACCS2-expressing cells (t-test p≤10-5), revealing the calcium specificity of $T_1$-weighted imaging signals obtained with ManICS1-AM inside living cells.

Example 4

ManICS1-AM Permits Detection of Deep Brain Activation in Rats

To determine whether ManICS1-AM could enable detection of intracellular calcium signals in vivo, the probe was injected into the brains of adult rats and responses were examined to stimulation with potassium ions, which induce neural depolarization and calcium concentration changes in brain tissue. Intracranial infusion of ManICS1-AM into the striatum resulted in substantial $T_1$-weighted MRI signal enhancement over a 4 mm diameter region around the injection site, as well as more remote tissue along the ventricles (FIGS. 8A and 8B). The contrast enhancement persisted for over 90 min without significant loss of signal (t-test p=0.42, n=4) (FIG. 8C), differing markedly from the behavior of hydrophilic MRI contrast agents that do not enter cells and that typically clear from the rodent brain within two hours.

Infusion of artificial cerebrospinal fluid (aCSF) formulated isotonically with 125 mM KCl elicited a robust signal change proximal to the infusion site in ManICS1-AM-infused brain areas (FIG. 8D). The ManICS1-dependent signal rose quickly, with an average signal change of 5.8±1.2% at stimulus offset that subsided slowly to baseline after the KCl infusion stopped (FIG. 8E). KCl injection in the presence of the calcium-insensitive contrast agent MnL1F—a close variant of the soluble cell-permeable MnL1 chelate—or infusion of standard aCSF containing 125 mM NaCl in the presence of ManICS1-AM elicited negligible mean responses of −0.2±0.8% and 1.2±1.2%, respectively, at stimulus offset with respect to baseline. The signal change observed under the ManICS1-AM $K^+$ stimulation condition differed significantly from signals observed under both control conditions (t-test p≤0.016, n=5) (FIG. 8F), consistent with the expected calcium-sensing mechanism of ManICS1 and with results obtained in cells.

These experiments thus demonstrate a cell-permeable manganese-based MRI contrast agent that emulates properties of fluorescent probes for cytosolic $Ca^{2+}$ imaging, and that can detect signaling events in deep tissue. The ManICS1 calcium sensor introduced here incorporates membrane-permeable building blocks and can exploit the AM ester-based approach for cell labeling and cytosolic trapping of the probe. Upon internalization, ManICS1-AM reports calcium levels consistent with readouts from optical calcium sensors and compatible with $T_1$-weighted functional MRI in rat brain, suggesting that the new probe could be used for spatiotemporal mapping of calcium signaling processes previously accessible only to optical imaging approaches, but with the expanded depth and field of view afforded by MRI.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A sensor comprising the structure, Y-L-Z, wherein:
Y is an analyte binding moiety;
L is a linker that covalently links Y and Z; and
Z is of the formula:

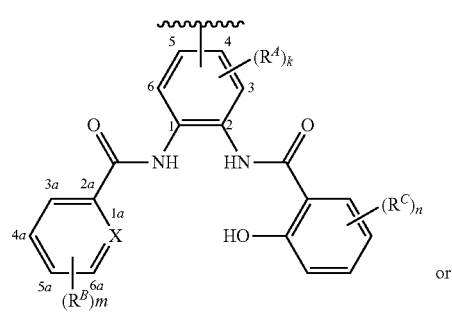

or

-continued

[Chemical structure diagram showing metal complex with pyridine and phenol groups, labeled with positions 1-6, 3a-6a, 1a-2a, substituents $(R^A)_k$, $(R^B)_m$, $(R^C)_n$, and central metal M]

wherein:
  M is metal ion;
  X is N;
  each instance of $R^A$ is independently halogen, unsubstituted $C_{1-6}$ alkyl, $C_{1-6}$ alkyl substituted with one or more instances of halogen, oxo, or —$OR^a$;
  each instance of $R^a$ is independently unsubstituted $C_{1-6}$ alkyl or $C_{1-6}$ alkyl substituted with one or more instances of halogen;
  k is 0, 1, 2, or 3;
  each instance of $R^B$ is directly attached to any one of the 3a- to 6a-positions and is independently halogen, unsubstituted $C_{1-6}$ alkyl, $C_{1-6}$ alkyl substituted with one or more instances of halogen, oxo, or —$OR^a$, or two instances of $R^B$ are joined to form a phenyl ring, wherein the phenyl ring formed by joining two instances of $R^B$ is unsubstituted or substituted with 1, 2, 3, or 4 instances of substituents independently selected from the group consisting of halogen, —$OR^a$, unsubstituted $C_{1-6}$ alkyl, and $C_{1-6}$ alkyl substituted with one or more instances of halogen;
  m is 0, 1, 2, 3, or 4;
  each instance of $R^c$ is independently halogen, unsubstituted $C_{1-6}$ alkyl, $C_{1-6}$ alkyl substituted with one or more instances of halogen, oxo, or —$OR^a$, or two instances of $R^c$ are joined to form a phenyl ring, wherein the phenyl ring formed by joining two instances of $R^c$ is unsubstituted or substituted with 1, 2, 3, or 4 instances of substituents independently selected from the group consisting of halogen, —$OR^a$, unsubstituted $C_{1-6}$ alkyl, and $C_{1-6}$ alkyl substituted with one or more instances of halogen; and
  n is 0, 1, 2, 3, or 4.

2. The sensor of claim 1, wherein the sensor further comprises an additional Y, Z, L, -L-Y, or -L-Z covalently bound to Y or Z.

3. The sensor of claim 1, wherein M is a paramagnetic metal ion.

4. The sensor of claim 1, wherein the analyte is a cell signaling ion.

5. The sensor of claim 4, wherein the cell signaling ion is a cation selected from the group consisting of: Calcium$^{2+}$, Sodium$^+$, Potassium$^+$, Magnesium$^{2+}$, and Zinc$^{2+}$.

6. The sensor of claim 1, wherein the analyte binding moiety contains at least one aromatic group.

7. The sensor of claim 1, wherein the analyte binding moiety contains at least one aromatic group selected from the group consisting of monocyclic aryl, bicyclic aryl, monocyclic heteroaryl, and bicyclic heteroaryl.

8. The sensor of claim 1, wherein Z has a planar configuration when chelating a paramagnetic metal ion.

9. The sensor of claim 1, wherein Z is of the formula:

[Chemical structure diagram similar to prior, with positions 1-6, 3a-6a, substituents $(R^A)_k$, $(R^B)_m$, $(R^C)_n$, and central metal M]

10. The sensor of claim 1, wherein the analyte binding moiety comprises a selective calcium chelating moiety derived from 1,2-bis(2-aminophenoxy)ethane-N,N, N',N'-tetraacetic acid (BAPTA).

11. The sensor of claim 10, wherein the selective calcium chelating moiety derived from BAPTA does not comprise the moiety —C(=O)OH.

12. The sensor of claim 9, wherein the analyte binding moiety is of the formula:

[Chemical structure diagram showing BAPTA-like moiety with two aromatic rings connected through $L^1$, bearing $(R^D)_p$ and $(R^E)_q$ substituents, with N-linked $-(\phantom{})_r$-C(=O)-O-R groups]

wherein:
  $L^1$ is unbranched $C_{2-8}$ alkylene, wherein:
    0, 1, 2, or 3 methylene units of the unbranched $C_{2-8}$ alkylene are independently replaced with O or N($R^F$), as valency permits, wherein each instance of $R^F$ is independently H or unsubstituted $C_{1-6}$ alkyl; and
    each methylene unit of the unbranched $C_{2-8}$ alkylene is independently unsubstituted or substituted with 1 or 2 instances of substituents independently selected from the group consisting of oxo, —$OR^a$, halogen, unsubstituted $C_{1-6}$, and $C_{1-6}$ alkyl substituted with one or more instances of halogen;
  each instance of $R^a$ is independently unsubstituted $C_{1-6}$ alkyl or $C_{1-6}$ alkyl substituted with one or more instances of halogen;
  each instance of $R^D$ is independently halogen, unsubstituted $_{1-6}$ alkyl, $_{1-6}$ alkyl substituted with one or more instances of halogen, or —$OR^a$;
  p is 0, 1, 2, or 3;
  each instance of $R^E$ is independently halogen, unsubstituted $C_{1-6}$ alkyl, $C_{1-6}$ alkyl substituted with one or more instances of halogen, or —$OR^a$;

q is 0, 1, 2, 3, or 4;
each instance of r is independently 0, 1, 2, or 3;
each instance of R is independently H or substituted or unsubstituted $C_{1-6}$ alkyl.

13. The sensor of claim 9, wherein the analyte binding moiety is a polyaminocarboxylate chelator.

14. The sensor of claim 13, wherein the polyaminocarboxylate chelator is selected from the group consisting of ethylenediaminetetraacetic acid (EDTA), ethylene glycol-bis(β-aminoethyl ether)-N,N,N', N'-tetraacetic acid (EGTA), diethylenetriaminepentaacetic acid (DTPA), 2-[(2-amino-5-methylphenoxy)methyl]-6-methoxy-8-aminoquinoline-N,N,N',N'-tetraacetic acid (quin-2), 1-(2-nitro-4,5-dimethoxyphenyl)-1,2-diaminoethane-N,N,N',N'-tetraacetic acid (DM-nitrophen), and o-aminophenol-N,N,O-triacetic acid (APTRA).

15. The sensor of claim 9, wherein the analyte binding moiety is a metal ion-selective crown ether.

16. The sensor of claim 1, wherein the linker, L, is an unbranched $C_{4-40}$ alkylene, unbranched C $C_{4-40}$ alkenylene, or unbranched $C_{4-40}$ alkynylene, wherein:
0, 1, or more methylene units of the unbranched $C_{4-40}$ alkylene, unbranched $C_{4-40}$ alkenylene, or unbranched $C_{4-40}$ alkynylene are independently replaced with O, N, N($R^F$), C(=O)O, C(=O)$NR^F$, S, optionally substituted carbocyclyl, optionally substituted heterocyclyl, optionally substituted aryl, or optionally substituted heteroaryl as valency permits, wherein each instance of $R^F$ is independently H or unsubstituted $C_{1-6}$ alkyl;
each methylene unit of the unbranched $C_{4-40}$ alkylene, unbranched $C_{4-40}$ alkenylene, or unbranched $C_{4-40}$ alkynylene is independently unsubstituted or substituted with 1 or 2 instances, as valency permits, of substituents independently selected from the group consisting of oxo, —$OR^a$, halogen, unsubstituted $C_{1-6}$ alkyl, and $C_{1-6}$ alkyl substituted with one or more instances of halogen; and each instance of $R^a$ is independently unsubstituted $C_{1-6}$ alkyl or $C_{1-6}$ alkyl substituted with one or more instances of halogen.

17. The sensor of claim 3, wherein M is an ion of iron, nickel, manganese, copper, gadolinium, dysprosium, or europium.

18. The sensor of claim 3, wherein M is $Mn^{2+}$.

19. The sensor of claim 1, wherein L is of the formula:

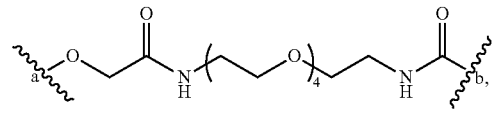

wherein:
the position a is directly attached to Z; and
the position b is directly attached to the analyte binding moiety.

20. The sensor of claim 1, wherein the sensor is of the formula:

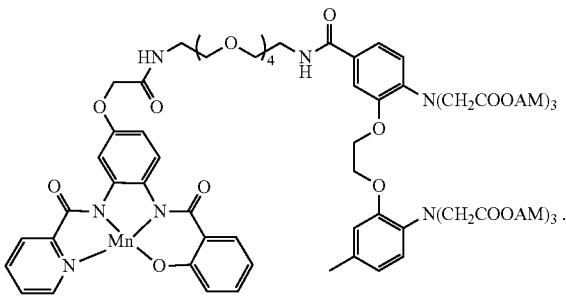

* * * * *